United States Patent [19]

Atwell et al.

[11] Patent Number: 4,603,125
[45] Date of Patent: Jul. 29, 1986

[54] SUBSTITUTED O-PHENYLENEDIAMINE ACRIDINE COMPOUNDS HAVING ANTITUMOR ACTIVITY

[75] Inventors: Graham J. Atwell; Bruce C. Baguley; William A. Denny; Gordon W. Rewcastle, all of Auckland, New Zealand

[73] Assignee: Development Finance Corporation of New Zealand, Wellington, New Zealand

[21] Appl. No.: 551,329

[22] Filed: Nov. 14, 1983

Related U.S. Application Data

[63] Continuation-in-part of Ser. No. 496,621, May 20, 1983, abandoned.

[30] Foreign Application Priority Data

May 24, 1982 [NZ] New Zealand .............. 200715

[51] Int. Cl.$^4$ ............... A61K 31/47; A61K 31/675; C07D 219/10; C07F 9/64
[52] U.S. Cl. ............................... 514/80; 514/280; 514/297; 546/23; 546/70; 546/106; 560/24; 564/50; 564/86; 564/91; 564/92; 564/99
[58] Field of Search .............. 546/106, 70; 424/257; 514/280, 297

[56] References Cited

U.S. PATENT DOCUMENTS

4,366,318 12/1982 Cain et al. .............. 546/106
4,472,582 9/1984 Cain et al. .............. 546/106
4,479,000 10/1984 Rewcastle et al. ........ 526/23

FOREIGN PATENT DOCUMENTS

0095355 11/1983 European Pat. Off. .

OTHER PUBLICATIONS

Cain, et al., J. Med. Chem., vol. 18, No. 11, pp. 1110–1117 (1975).
Cain, et al., Mol. Pharmacol., vol. 12, No. 6, pp. 1027–1035 (1976).
Ferguson, et al., J. Med. Chem., vol. 23, No. 3, pp. 269–274 (1980).
Baguley, et al., Eur. J. Cancer, vol. 17, No. 6, pp. 671–679 (1981).
Denny, et al., J. Med. Chem., vol. 25, No. 3, pp. 276–315 (03/82).
Atwell, et al., J. Med. Chem., vol. 27, No. 3, pp. 367–372 (1984).

Primary Examiner—Donald G. Daus
Assistant Examiner—Diana G. Rivers
Attorney, Agent, or Firm—Pennie & Edmonds

[57] ABSTRACT

Compounds represented by the general formula (I):

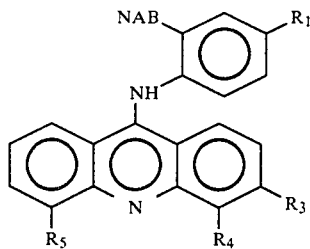

in which $R_1$ represents

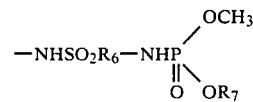

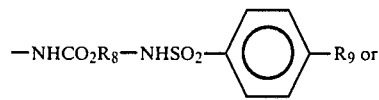

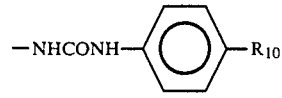

A and B each represent H or a lower alkane optionally substituted with amino and/or hydroxyl functions, except that A and B are not both H; $R_3$ represents H, $OCH_3$, $CH_3$, halogen, $NH_2$, $NO_2$, $NHCH_3$, $N_3(CH_3)_2$, $N_3$, $NHCOCH_3$, $NHCOOCH_3$, $N(CH_3)COOCH_3$, $CONH_2$ or $CONHCH_3$; $R_4$ represents H, alkyl, O-alkyl, $CONH_2$, $CONHCH_3$ or $CONHCH_2CONHCH_3$, except that $R_3$ and $R_4$ taken together can represent $-C=CH-CH=N-$; $R_5$ represents H, alkyl, O-alkyl, $CONH_2$, $CONHCH_3$ or $CONH_2CH_2$ $CONHCH_3$; $R_6$ represents lower alkyl; $R_7$ represents $CH_3$ or $C_6H_5$ (phenyl); $R_8$ represents lower alkyl or $C_6H_5$ (phenyl); $R_9$ represents H, $NHCOCH_3$, $NH_2$ or $N=CHN(CH_3)_2$; and $R_{10}$ represents H or $NH_2$; and the acid addition salts thereof, possess antibacterial and antitumour properties.

23 Claims, No Drawings

SUBSTITUTED O-PHENYLENEDIAMINE ACRIDINE COMPOUNDS HAVING ANTITUMOR ACTIVITY

CROSS REFERENCE TO RELATED APPLICATION

This application is a continuation-in-part of U.S. application Ser. No. 496,621, filed May 20, 1983, now abandoned.

BACKGROUND TO THE INVENTION

A number of derivatives of acridine have recently been studied for antitumour activity. Earlier work with simple 9-anilinoacridines showed that 4'-(9-acridinylamino) methanesulphonanilide or AMSA had good antitumour activity on the mouse L1210 leukemia model (G. J. Atwell, B. F. Cain and R. N. Seelye, *J. Med. Chem.*, 15, 611–615 (1972). A study of the effects of various substituents placed on the anilino ring on biological activity revealed that a methoxy group at the 3'-position, meta to the methanesulfonamide, increased dose potency, and led to the clinical agent 4'-(9-acridinylamino)methanesulphon-m-anisidide, m-AMSA or amsacrine. (B. F. Cain and G. J. Atwell, *Europ. J. Cancer*, 10, 539–549 (1974) and see also the following articles: B. F. Cain, G. J. Atwell and W. A. Denny, *J. Med. Chem.*, 18, 1110–1117 (1975); B. F. Cain, W. R. Wilson and B. C. Baguley, *Molecular Pharmacology*, 12, 1027–1035 (1976); B. F. Cain, G. J. Atwell and W. A. Denny, *J. Med. Chem.*, 19, 772–777 (1976); B. F. Cain and G. J. Atwell, *J. Med. Chem.*, 19, 1409–1416 (1976); M. J. Waring, *Europ.J.Cancer*, 12, 995–1001 (1976); B. C. Baguley, W. R. Wilson, L. R. Ferguson and B. F. Cain, *Current Chemotherapy*, pp. 1210–1212 (1978); W. A. Denny, G. J. Atwell and B. F. Cain, *J.Med.Chem.*, 21, 5–10 (1978).)

The antitumour activity of a large range of AMSA and m-AMSA analogues containing variously substituted acridine and anilide nuclei has now been investigated, see for example G. J. Atwell, B. F. Cain and R. N. Seelye, *J.Med.Chem.*, 15, 611–615 (1972); B. F. Cain, R. N. Seelye and G. J. Atwell, *J.Med.Chem.*, 17, 922–930 (1974); B. F. Cain, G. J. Atwell and W. A. Denny, *J.Med.Chem.*, 18, 1110–1117 (1975), and *J.Med.Chem.*, 19, 772–777 (1976); B. F. Cain and G. J. Atwell, *J.Med.Chem.*, 19, 1124–1129 and 1409–1416 (1976); G. J. Atwell, B. F. Cain and W. A. Denny, *J.Med.Chem.*, 20, 520–526, 987–996, 1128–1134, and 1242–1246 (1977); W. A. Denny, G. J. Atwell and B. F. Cain, *J.Med.Chem.*, 21, 5–10 (1978); W. A. Denny and B. F. Cain, *J.Med.Chem.*, 21, 430–437 (1978); B. F. Cain, B. C. Baguley and W. A. Denny, *J.Med.Chem.*, 21, 658–668 (1978); L. R. Ferguson and W. A. Denny, *J.Med.Chem.*, 22, 251–255 (1979); W. A. Denny, G. J. Atwell and B. F. Cain, *J.Med.Chem.*, 22, 1453–1460 (1979); L. R. Ferguson and W. A. Denny, *J.Med.Chem.*, 23, 269–274 (1980); B. C. Baguley, W. A. Denny, G. J. Atwell and B. F. Cain, *J.Med.Chem.*, 24, 170–177 and 520–525 (1981); L. R. Ferguson and B. C. Baguley, *Mutation Research*, 82, 31–39 (1981); W. A. Denny, B. F. Cain, G. J. Atwell, C. Hansch, A. Panthananickal and A. Leo *J.Med.Chem.*, 25, 276–315 (1982); G. W. Rewcastle, B. C. Baguley and B. F. Cain, *J.Med.Chem.*, 25, 1231–1235 (1982); B. F. Cain, G. J. Atwell, B. C. Baguley and W. A. Denny, U.S. Pat. No. 4,472,582, issued Sept. 18, 1984; and B. F. Cain and G. J. Atwell, U.S. Pat. No. 4,366,318, issued Dec. 28, 1982.

During this work it was found that a number of groups other than methoxy placed at the 3'-position (e.g., F, Cl, $NO_2$, Br) abolished activity and provided nontoxic compounds. Even groups of a similar steric and electronic nature to methoxy (e.g., $-CH_3$, $-OCH_2CH_3$, $-OH$ and especially $-NH_2$) provided compounds of decreased activity and (except for the $-OH$ group) decreased potency. The strongly electronegative amino group ($NH_2$) did not increase potency or activity over that of the unsubstituted AMSA (B. F. Cain, G. J. Atwell and W. A. Denny, *J.Med.Chem.*, 18, 1110–1117, 1975).

SUMMARY OF THE INVENTION

We have now found unexpectedly that the presence of a 3'-methylamino group, in contrast to the electronically-similar 3'-$NH_2$ group, furnishes a compound (compound 1 of Table I) with increased potency and antitumour activity compared to the unsubstituted AMSA and the 3'-methoxy derivative m-AMSA (amsacrine). Furthermore, we have also found unexpectedly that the presence of a 3'-alkylamino or 3'-dialkylamino group provides a general class of o-phenylenediamine derivatives possessing high potency and antitumour activity.

It is the object of the present invention to provide novel derivatives of o-phenylenediamine substituted with heterocyclic groups, and methods for the preparation of these compounds. These novel compounds possess antibacterial and antitumour properties, and thus may be useful as antibacterial and antitumour agents.

DESCRIPTION OF THE INVENTION

The novel class of substituted o-phenylenediamine compounds of the present invention is represented by the general formula (I):

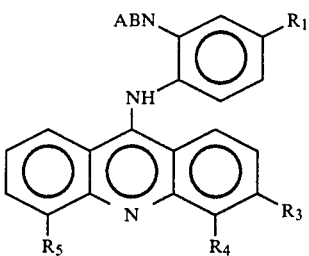

in which $R_1$ represents

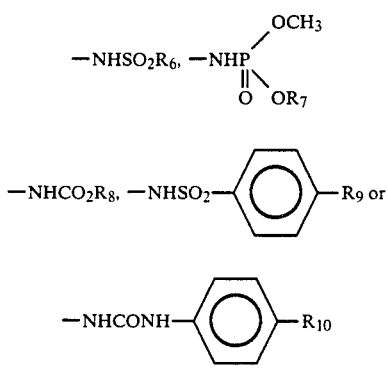

A and B each represents H or a lower alkane optionally substituted with amino and/or hydroxyl group, except that A and B are not both H; $R_3$ represents H, $OCH_3$, $CH_3$, halogen, $NH_2$, $NO_2$, $NHCH_3$, $N_3(CH_3)_2$, $N_3$, $NHCOCH_3$, $NHCOOCH_3$, $N(CH_3)COOCH_3$, $CONH_2$ or $CONHCH_3$; $R_4$ represents H, alkyl, O-alkyl, $CONH_2$, $CONHCH_3$ or $CONHCH_2CONHCH_3$, except that $R_3$ and $R_4$ taken together can represent —C=CH—CH—N—; $R_5$ represents H, alkyl, O-alkyl, $CONH_2$, $CONHCH_3$ or $CONH_2CH_2 CONHCH_3$; $R_6$ represents lower alkyl; $R_7$ represents $CH_3$ or $C_6H_5$ (phenyl); $R_8$ represents lower alkyl or $C_6H_5$ (phenyl); $R_9$ represents H, $NHCOCH_3$, $NH_2$ or $N=CHN(CH_3)_2$; and $R_{10}$ represents H or $NH_2$; and the acid addition salts thereof.

When $R_6$ or $R_8$ represents a lower alkyl group, or when A or B represents an optionally substituted lower alkane, the group may contain from 1 to 6 carbon atoms but is preferably methyl.

A preferred class of compounds of the above general formula (I) is that in which $R_1$ represents $NHSO_2CH_3$, A represents H, B represents $CH_3$, $R_3$ represents H, $CH_3$, $OCH_3$ or halogen, and $R_4$ and $R_5$ each represents H, $CH_3$ or $OCH_3$. A more preferred subclass of these compounds is that in which $R_3$ represents H, $CH_3$, F or Cl, $R_4$ represents H, and $R_5$ represents $CH_3$.

A second preferred class of compounds is that in which $R_1$ represents $NHSO_2CH_3$, A and B both represent $CH_3$, $R_3$ represents H, $CH_3$, $OCH_3$ or halogen, and $R_4$ and $R_5$ each represents H, $CH_3$, $OCH_3$ or $CONHCH_3$. A more preferred subclass of these compounds is that in which $R_3$ represents H or $OCH_3$, $R_4$ represents H or $CH_3$, and $R_5$ represents H, $CH_3$ or $CONHCH_3$.

A third preferred class of compounds is that in which $R_1$ represents $NHCO_2CH_3$, A represents H, B represents $CH_3$, $R_3$ represents H or $CH_3$, $R_4$ represents H, and $R_5$ represents H or $CH_3$.

The compounds of formula (I) form addition salts with acids. As examples of acid addition salts there may be mentioned the pharmaceutically acceptable acid addition salts formed with mineral acids and organic acids, for example, hydrochloric, hydrobromic, lactic, methanesulphonic, D-gluconic and 2-hydroxyethanesulphonic acids.

The compounds of formula (I) and acid addition salts thereof may be prepared by a process which comprises the acid-catalyzed coupling of a substituted heterocycle of the general formula (II):

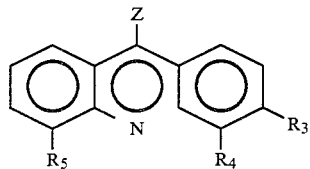

II where $R_3$, $R_4$ and $R_5$ represent groups as defined for formula (I), and Z represents any suitable leaving group (e.g., methoxy, phenoxy, alkylthio or halogen but preferably chloro) with one of the following o-phenylenediamine derivatives:

an o-phenylenediamine alkanesulphonamide of the general formula (III),

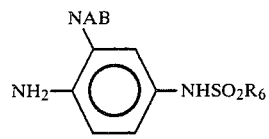

III where A and B each represents H or a lower alkane optionally substituted with amino and/or hydroxyl groups, except that A and B are not both H, and $R_6$ represents lower alkyl;

an o-phenylenediamine phosphoramidate of the general formula (IV),

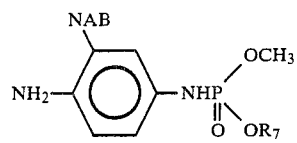

IV where A and B each represents H or a lower alkane optionally substituted with amino and/or hydroxyl groups, except that A and B are not both H, and $R_7$ represents $CH_3$ or $C_6H_5$ (phenyl);

an o-phenylenediamine carbamate of the general formula (V)

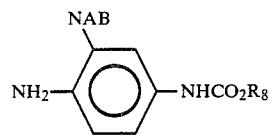

V where A and B each represents H or a lower alkane optionally substituted with amino and/or hydroxyl groups, except that A and B are not both H, and $R_8$ represents lower alkyl or phenyl;

an o-phenylenediamine benzenesulphonamide of the general formula (VI),

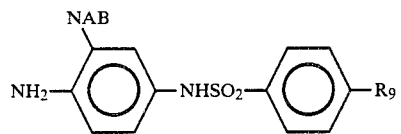

VI where A and B each represent H or a lower alkane optionally substituted with amino and/or hydroxyl groups, except that A and B are not both H, and $R_9$ is H, $NHCOCH_3$, $NH_2$ or $N=CHN(CH_3)_2$;

an o-phenylenediamine phenylurea of the general formula (VII),

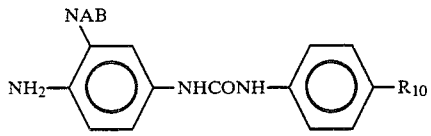

VII where A and B each represents H or a lower alkane optionally substituted with amino and/or hydroxyl groups, except that A and B are not both H, and $R_{10}$ is H or $NH_2$; in an anhydrous solvent and, if desired, converting an acid addition salt of a compound formula (I) into a free base compound of formula (I) and/or converting a compound of formula (I) into an acid addition salt thereof.

The acid-catalyzed coupling reaction of the substituted heterocycle with the appropriate o-phenylenediamine is performed in an anhydrous solvent, for example, methanol, ethanol, 2-ethoxyethanol or N-methylpyrrolidone, with methanol being the preferred solvent. The reaction is preferably performed at temperatures between 30° and 100° C.

The acid addition salts are prepared by contacting the free base form with an equivalent amount of the desired acid in the conventional manner. The free base forms may be regenerated by treating the salt form with a base. For example, dilute aqueous base solutions may be utilized. Dilute aqueous potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The coupling of a 9-chloroheterocycle of formula (II, Z=Cl) with an appropriate o-phenylenediamine may be performed according to the following procedure which is given as an example of the coupling reaction of the invention.

A methanolic solution of 1.1 equivalents of one of the sulfonanilide, phosphoramidate, carbamate, benzenesulfonamide or diphenylurea o-phenylenediamine derivatives (III–VII) (preferably obtained in situ by hydrogenation of the nitro precursor over palladium on charcoal and filtration of the catalyst) is combined with one equivalent of the appropriate 9-chloroheterocycle dissolved or suspended in methanol, and a drop of concentrated hydrochloric acid is added to initiate the reaction (as evidenced by the appearance of a deep red coloration). At the completion of the coupling reaction (5–10 minutes at 20° C. for the unsubstituted 9-chloroacridine and after 15 minutes reflux for less soluble substituted derivatives) the solution is concentrated to small volume under vacuum, and allowed to stand (ethyl acetate being added if necessary) until crystallization is complete. The product hydrochloride salt can be purified further if necessary by recrystallization from methanol-ethyl acetate.

Conversion of the hydrochloride salt to the free base can be achieved by the addition of 1.1 equivalents of aqueous $KHCO_3$ to a solution of the salt in aqueous methanol, followed by rapid dilution with water to precipitate the base, which is liable to rapid oxidative breakdown in solution. The dried free base can be converted to other acid addition salts by dissolution in dilute methanolic solutions of the appropriate acid, followed by dilution of the solution with ethyl acetate.

The 9-chloroheterocycles of formula (II, Z=Cl) may be prepared using published methods (e.g., B. F. Cain, G. J. Atwell and W. A. Denny, *J.Med.Chem.*, 18, 1110–1117, 1975).

The 9-bromoheterocycles of formula (II, Z=Br) can be similarly prepared from either appropriate diphenylamine-2-carboxylic acids by treatment with phosphoryl bromide, or from the acridone by reaction with thionyl bromide. 9-Phenoxy and 9-methoxy heterocycles can be prepared by the methods given in Albert, "The Acridines", Second Edition, Edward Arnold Ltd., London (1966). 9-Alkythio heterocycles, and the precursor 9-acridanthiones, can be prepared by the methods cited in E. F. Elslager et al, *J.Med.Chem.*, 14, 782–788 (1971).

The intermediate o-phenylenediamine derivatives of the formulae (III) to (VII) are novel compounds and form part of the present invention. They can be represented by the formula (VIII)

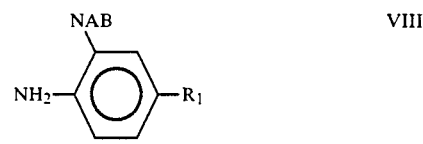

where $R_1$, A and B are as defined for formula (I).

In each of the classes of compounds of formula (III) to (VII) it is preferred that A is H or $CH_3$ and B is $CH_3$ or $CH_2CH_2OH$. It is also preferred that $R_6$ in formula (III) and $R_8$ in formula (V) are $CH_3$. The o-phenylenediamine derivatives (III–VII) may be prepared from 4-nitro-3-haloacetanilide (IX, where X is halogen, preferably Cl or Br) by the method of Scheme I, and this general process also forms part of the present invention. In Scheme I, A and B are as defined above, and Y is as defined below.

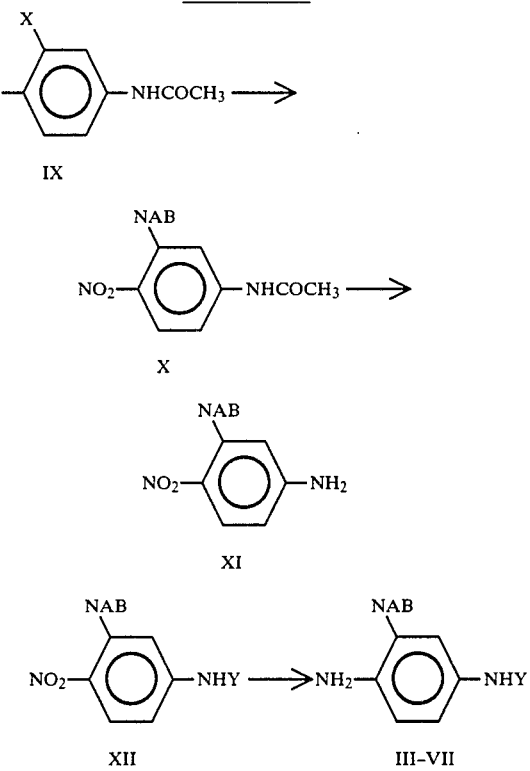

Treatment of the 4-nitro-3-haloacetanilide (IX) with neat amine HNAB at 100° C. for 2–6 hrs. (under pressure for the more volatile amines) provides compounds (X), which are deacylated in ethanolic HCl to give (XI). Treatment of (XI) in a suitable solvent (preferably pyridine) with either 1.1 equivalents (if A and B are not hydroxyalkyl) or 2.2 equivalents (if A or B is hydroxyalkyl) of respectively alkyl—$SO_2Cl$, $(CH_3)_2$ P(O)Br, $(CH_3O)$ (PhO) P(O)Br, alkyl—OCOCl, phenyl—O-COCl,

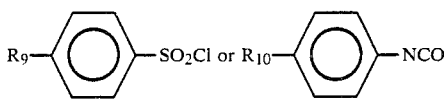

provides products (XII), where Y is respectively SO₂ alkyl, P(O) (OCH₃)₂, P(O) (OCH₃) (OPh), CO₂ alkyl, CO₂ phenyl,

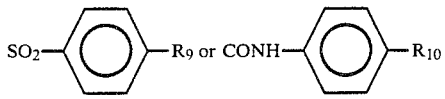

(For the cases where A or B is hydroxyalkyl, mild acid hydrolysis in ethanolic HCl to remove O-acyl functions is carried out). Palladium/carbon catalyzed hydrogenation of the nitrocompound (XII) in suitable solvents, preferably methanol, provides and o-phenylenediamine derivatives (III–VII).

For the lower alkylamine and hydroxy-alkylamine, particularly for the methylamine and ethanolamine, values for NAB, a more convenient process for the preparation of compounds (XII) (where A is H and B is CH₃, CH₂CH₃, CH₂CH₂CH₃ or CH₂CH₂OH) is shown in Scheme II, and this general process also forms part of the present invention. In Scheme II, B and Y are as defined above, and X represents halogen, preferably Cl or Br.

SCHEME II

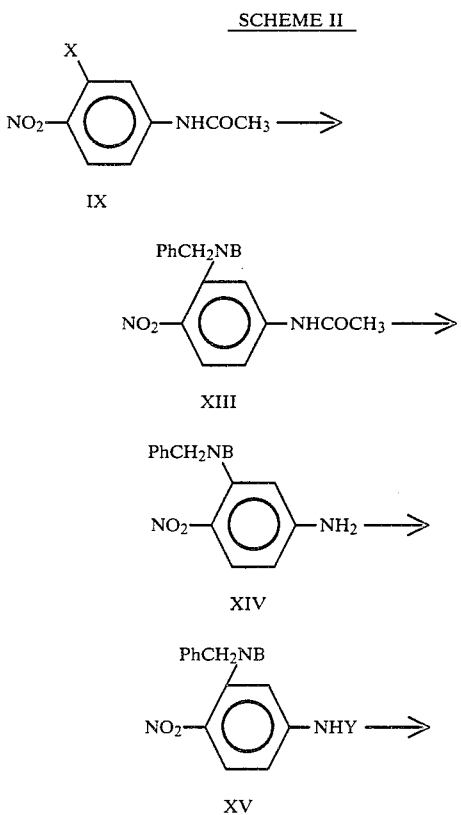

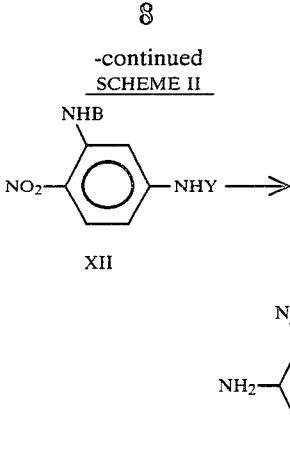

Treatment of the 4-nitro-3-haloacetanilide (IX) with either neat N-benzylalkylamine or N-benzylethanolamine provides (XIII), which is deacylated in ethanolic KOH to give (XIV). Treatment of (XIV) in a suitable solvent (preferably pyridine) with either 1.1 equivalents (if B is alkyl) or 2.2 equivalents (if B is CH₂CH₂OH) of respectively alkyl—SO₂Cl, (CH₃O)₂ P(O)Br, (CH₃O) (PhO) P(O)Br, alkyl—OCOCl, phenyl—OCOCl,

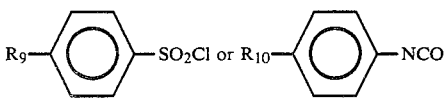

provides products (XV), where Y is respectively SO₂ alkyl, P(O) (OCH₃)₂, P(O) (OCH₃) (OPh), CO₂ alkyl, CO₂ phenyl,

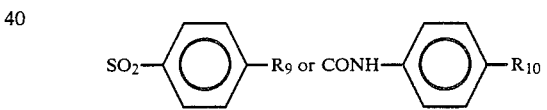

Mild acid hydrolysis of these products in ethanolic HCl removes the benzyl protecting group (and in the cases where B is CH₂CH₂OH also the acyl function from the ethanolamine) to provide (XII) which can be hydrogenated over palladium/carbon in suitable solvents (preferably methanol) to provide the o-phenylenediamine derivatives (III–VII), where A is H, and B is CH₃, CH₂CH₃, CH₂CH₂CH₃ or CH₂CH₂OH.

For the particular case of o-phenylenediamine derivatives of general formulas (III) and (VI), where Y is SO₂CH₃ or

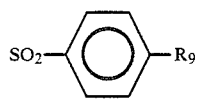

an alternative method of preparation is outlined in Scheme III, and this process also forms part of the present invention. In Scheme III, A and B are as defined above, and X represents halogen, preferably Cl or Br.

SCHEME III

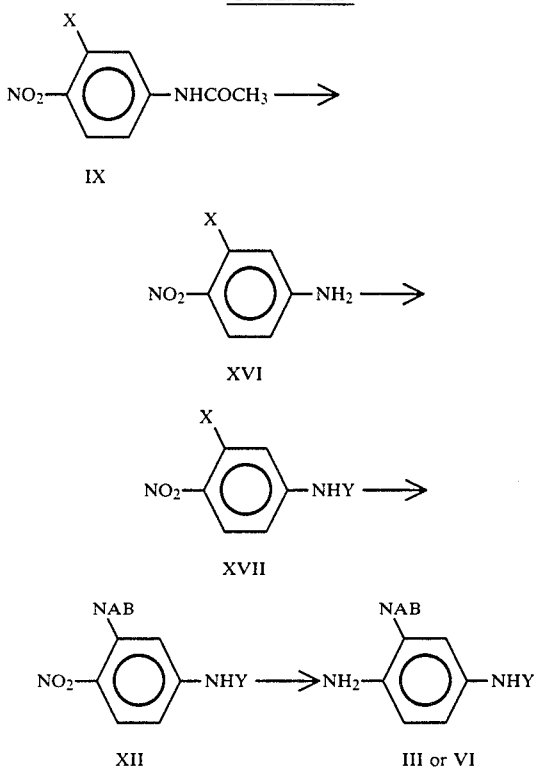

Mild acid hydrolysis of 4-nitro-3-haloacetanilide (IX) provides the amine (XXI), which is coupled with an appropriate sulfonyl chloride in a suitable solvent (preferably pyridine) to give (XVII). Treatment of this compound with a suitable amine HNAB yields compounds (XII), which can be catalytically hydrogenated over palladium/carbon in a suitable solvent (preferably methanol) to provide the o-phenylenediamine derivatives (III) or (VI).

The following Tables I and II set out physical data for sixty-four compounds within the general formula (I), representative of it, and preparable by the processes of the invention. In Table I the following terms and abbreviations are used:

MW = molecular weight

MP = melting point of the reported acid addition salt in °C.

Rm = a measure of the compound's lipophilic-hydrophilic balance from reversed phase partition chromatography. Rm is linearly related to partition coefficients obtained in the 1-octanol/water system.

A, B, $R_1$, $R_3$, $R_4$ and $R_5$ refer to formula (I). $R_3$, $R_4$, $R_5$ are all H unless otherwise specified.

TABLE I

| No. | $R_1$ | B (A = H unless specified) | $R_3$, $R_4$, $R_5$ | Formula | MP | MW | Rm |
|---|---|---|---|---|---|---|---|
| 1 | NHSO₂CH₃ | CH₃ | H | $C_{21}H_{20}N_4O_2S \cdot HCl$ | 261–263 | 427.5 | 0.17 |
| 3 | " | " | 3-CH₃ | $C_{22}H_{22}N_4O_2S \cdot HCl$ | 295–296 | 443 | 0.39 |
| 4 | " | " | 3-OCH₃ | $C_{22}H_{22}N_4O_3S \cdot HCl$ | 231–233 | 458.7 | 0.21 |
| 5 | " | " | 3-F | $C_{21}H_{19}FN_4O_2S \cdot 2HCl$ | 250–255 | 483.2 | 0.28 |
| 6 | " | " | 3-Cl | $C_{21}H_{19}ClN_4O_2S \cdot 2HCl$ | 250–255 | 499.7 | 0.36 |
| 7 | " | " | 3-Br | $C_{21}H_{19}BrN_4O_2S \cdot HCl$ | 299–300 | 508 | 0.34 |
| 8 | " | " | 3-I | $C_{21}H_{19}IN_4O_2S \cdot 2HCl$ | 240(d) | 572.1 | 0.35 |
| 9 | " | " | 3-NO₂ | $C_{21}H_{19}N_5O_4S \cdot HCl \cdot \frac{1}{2}H_2O$ | 275–276 | 482.9 | 0.04 |
| 10 | " | " | 3-NHCH₃ | $C_{22}H_{23}N_5O_2S \cdot HCl$ | 261–263 | 457.8 | 0.18 |
| 11 | " | " | 3-NHCOOCH₃ | $C_{23}H_{23}N_5O_4S \cdot HCl$ | 243–245 | 501.8 | 0.13 |
| 12 | " | " | 4-CH₃ | $C_{22}H_{22}N_4O_2S \cdot HCl \cdot \frac{1}{2}H_2O$ | 240–241 | 452 | 0.19 |
| 13 | " | " | 4-OCH₃ | $C_{22}H_{22}N_4O_3S \cdot HCl$ | 217–221 | 458.7 | 0.12 |
| 15 | " | " | 4-CONHCH₃ | $C_{23}H_{23}N_5O_3S \cdot 2HCl$ | 242–245 | 484.5 | 0.07 |
| 16 | " | " | 3-CH₃,5-CH₃ | $C_{23}H_{24}N_4O_2S \cdot HCl$ | 261–263 | 457.0 | 0.38 |
| 17 | " | " | 3-OCH₃,5-CH₃ | $C_{23}H_{24}N_4O_3S \cdot HCl \cdot \frac{1}{2}H_2O$ | 276–277 | 482 | 0.31 |
| 18 | " | " | 3-F,5-CH₃ | $C_{22}H_{21}FN_4O_2S \cdot HCl$ | 255–260 | 460.8 | 0.31 |
| 19 | " | " | 3-Cl,5-CH₃ | $C_{22}H_{21}ClN_4O_2S \cdot HCl$ | 276–278 | 475.0 | 0.40 |
| 20 | " | " | 3-Cl,5-OCH₃ | $C_{22}H_{21}ClN_4O_3 \cdot 2HCl$ | 276–278 | 490.0 | |
| 21 | " | " | 3-Br,5-CH₃ | $C_{22}H_{21}BrN_4O_2 \cdot HCl$ | 274–276 | 525.5 | 0.38 |
| 22 | " | " | 3-CH₃,5-OCH₃ | $C_{23}H_{24}N_4O_2 \cdot S \cdot HCl$ | 261–262 | 473.0 | 0.33 |
| 23 | " | " | 3-Cl,5-CONHCH₂ | $C_{23}H_{22}ClN_5O_3S \cdot HCl$ | 265–270 | 518.0 | 0.23 |
| 24 | " | " | 4-CH₃,5-CONHCH₃ | $C_{24}H_{25}N_5O_3S \cdot HCl$ | 249–251 | 500.0 | 0.23 |
| 25 | " | " | 4,5-diCH₃ | $C_{23}H_{24}N_4O_2S \cdot HCl \cdot \frac{1}{2}H_2O$ | 279–280 | 466 | 0.16 |
| 26 | " | " | 4,5-diOCH₃ | $C_{23}H_{24}N_4O_4S \cdot HCl$ | 268–272 | 487.2 | |
| 27 | " | CH₂CH₂OH | H | $C_{22}H_{22}N_4O_3S \cdot HCl$ | 270–271 | 459 | 0.07 |
| 28 | " | " | 3-Br | $C_{22}H_{21}BrN_4O_3S \cdot HCl$ | 272–273 | 538 | 0.11 |
| 29 | " | " | 4-CH₃ | $C_{23}H_{24}H_4O_3S \cdot HCl$ | 257–258 | 473 | 0.02 |
| 30 | " | CH₂CH(OH)CH₂OH | H | $C_{23}H_{24}N_4O_4S \cdot HCl$ | 254–256 | 489 | 0.30 |
| 31 | " | " | 4-CH₃ | $C_{24}H_{26}N_4O_4S \cdot HCl$ | 184–186 | 503 | 0.21 |
| 32 | " | A = B = CH₃ | H | $C_{22}H_{22}N_4O_2S \cdot HCl \cdot 0.5H_2O$ | 248–249 | 452 | 0.41 |
| 33 | " | " | 3-Cl | $C_{22}H_{21}ClN_4O_2S \cdot HCl$ | 267–270 | 491.2 | |
| 34 | " | " | 4-CH₃ | $C_{23}H_{24}N_4O_2S \cdot HCl \cdot \frac{1}{2}H_2O$ | 198–199 | 466 | 0.36 |
| 35 | " | " | 4-OCH₃ | $C_{23}H_{24}N_4O_3S \cdot HCl$ | 205–209 | 472.2 | |
| 36 | " | " | 4-CONHCH₃ | $C_{24}H_{25}N_5O_3S \cdot 2HCl$ | 202–205 | 464.3 | |
| 37 | " | " | 3-F,5-CH₃ | $C_{23}H_{23}FN_4O_2S \cdot HCl$ | 205–210 | 438.3 | |
| 38 | " | " | 3-Cl,5-CH₃ | $C_{23}H_{23}ClN_4O_2S \cdot 2HCl$ | 225–230 | 527.9 | |
| 39 | " | " | 3-Cl,5-OCH₃ | $C_{23}H_{23}ClN_4O_3S \cdot HCl$ | 205–210 | 469.8 | |
| 40 | " | " | 3-Cl,5-CONHCH₃ | $C_{24}H_{24}ClN_5O_3S \cdot HCl$ | 256–258 | 532.0 | |

TABLE I-continued

| No. | $R_1$ | B (A = H unless specified) | $R_3, R_4, R_5$ | Formula | MP | MW | Rm |
|---|---|---|---|---|---|---|---|
| 41 | " | " | 3-OCH$_3$,5-CH$_3$ | C$_{24}$H$_{26}$N$_4$O$_3$S.HCl | 255-256 | 485.8 | 0.44 |
| 42 | " | " | 4,5-diCH$_3$ | C$_{24}$H$_{26}$N$_4$O$_2$S.HCl | 255-257 | 470.8 | |
| 43 | " | " | 4,5-diOCH$_3$ | C$_{24}$H$_{26}$N$_4$O$_4$S.HCl | 210-213 | 500.8 | |
| 44 | " | " | 4-CH$_3$5-CONHCH$_3$ | C$_{25}$H$_{27}$N$_5$O$_3$S.HCl | 273-275 | 513.8 | 0.40 |
| 45 | " | A = CH$_3$ B = CH$_2$CH$_2$OH | H | C$_{23}$H$_{24}$N$_4$O$_3$S.HCl.½H$_2$O | 168-170 | 482 | 0.10 |
| 46 | " | " | 4-CH$_3$ | C$_{24}$H$_{26}$N$_4$O$_3$S.HCl | 215-217 | 487.0 | |
| 47 | NHP(O)(OCH$_3$)$_2$ | CH$_3$ | H | C$_{22}$H$_{23}$N$_4$O$_3$P.HCl.½H$_2$O | 230(d) | 467 | 0.32 |
| 48 | NHP(O)(OCH$_3$)$_2$ | " | 3-Br | C$_{22}$H$_{22}$BrN$_4$O$_3$P.HCl 0.5H$_2$O | 350(d) | 547 | 0.62 |
| 49 | NHP(O)(OCH$_3$)$_2$ | " | 4-CH$_3$ | C$_{23}$H$_{25}$N$_4$O$_3$P.HCl | 216-219 | 473 | 0.47 |
| 50 | NHCO$_2$CH$_3$ | " | H | C$_{22}$H$_{20}$N$_4$O$_2$.HCl 0.5H$_2$O | 268(d) | 417.9 | 0.51 |
| 51 | " | CH$_2$CH$_2$OH | H | C$_{23}$H$_{22}$N$_4$O$_3$.HCl | 240-242 | 434 | 0.39 |
| 52 | " | CH$_3$ | 3-CH$_3$ | C$_{23}$H$_{22}$N$_4$O$_2$.HCl | 272-274 | 423 | 0.78 |
| 53 | " | " | 3-F | C$_{22}$H$_{19}$FN$_4$O$_2$.HCl | 246-250 | 425.5 | 0.63 |
| 54 | " | " | 3-Cl | C$_{22}$H$_{19}$ClN$_4$O$_2$.HCl | 250(d) | 441 | 0.73 |
| 55 | " | " | 3-Br | C$_{22}$H$_{19}$BrN$_4$O$_2$.HCl | 270(d) | 488 | 0.70 |
| 56 | " | " | 3-Cl,5-CH$_3$ | C$_{23}$H$_{21}$ClN$_4$O$_2$.2HCl | >310 | 457.1 | 0.67 |
| 57 | " | " | 3-Br,5-CH$_3$ | C$_{23}$H$_{21}$BrN$_4$O$_2$.HCl | >310 | 501.2 | 0.69 |
| 58 | " | " | 4-CH$_3$ | C$_{23}$H$_{22}$N$_4$O$_2$.HCl 1.5H$_2$O | 283-285 | 449.9 | 0.56 |
| 59 | | A = B = CH$_3$ | H | C$_{23}$H$_{22}$N$_4$O$_2$.HCl | 260-262 | 422.9 | 0.56 |
| 60 | NHSO$_2$Ph | CH$_3$ | H | C$_{26}$H$_{22}$N$_4$O$_2$S.HCl | 294(d) | 491 | 0.55 |
| 61 | NHSO$_2$Ph | CH$_2$CH$_2$OH | H | C$_{27}$H$_{24}$N$_4$O$_3$S.HCl | 258(d) | 521 | 0.35 |
| 62 | NHSO$_2$Ph NH$_2$ p | CH$_3$ | H | C$_{26}$H$_{23}$N$_5$O$_2$S.HCl.½H$_2$O | 230(d) | 515 | 0.03 |
| 63 | NHSO$_2$Ph NH$_2$ p | " | 3-Br | C$_{26}$H$_{22}$BrN$_5$O$_2$S.HCl | 290(d) | 585 | 0.29 |
| 64 | NHSO$_2$Ph NH$_2$ p | " | 4-CH$_3$ | C$_{27}$H$_{25}$N$_5$O$_2$S.HCl.½H$_2$O | 265(d) | 529 | 0.13 |
| 65 | NHSO$_2$Ph NH$_2$ p | CH$_2$CH$_2$OH | H | C$_{27}$H$_{25}$N$_5$O$_3$S.HCl.H$_2$O | 260(d) | 554 | 0.18 |
| 66 | NHCOOPh | CH$_3$ | H | C$_{27}$H$_{22}$N$_4$O$_2$.HCl | 288-290 | 470.7 | 0.76 |

TABLE II

Elemental Analyses for the Compounds of Table I

| | | Found | | | | Calculated | | | |
|---|---|---|---|---|---|---|---|---|---|
| No. | Formula | C | H | N | Cl | C | H | N | Cl |
| 1 | C$_{21}$H$_{20}$N$_4$O$_2$S.HCl | 59.3 | 5.1 | 13.1 | 8.7 | 58.8 | 4.9 | 13.1 | 8.3 |
| 3 | C$_{22}$H$_{22}$N$_4$O$_2$S.HCl | 59.4 | 5.2 | 12.5 | 8.0 | 59.6 | 5.2 | 12.6 | 8.0 |
| 4 | C$_{22}$H$_{22}$N$_4$O$_3$S.HCl | 57.4 | 5.2 | 12.5 | 7.9 | 57.6 | 5.0 | 12.2 | 7.7 |
| 5 | C$_{21}$H$_{19}$FN$_4$O$_2$S.2HCl | 52.1 | 5.0 | 11.5 | 14.4 | 52.4 | 4.4 | 11.6 | 14.1 |
| 6 | C$_{21}$H$_{19}$ClN$_4$O$_2$S.2HCl | 50.8 | 4.2 | 11.3 | 20.8 | 50.8 | 4.2 | 11.3 | 20.8 |
| 7 | C$_{21}$H$_{19}$BrN$_4$O$_2$S.HCl | 50.2 | 4.3 | 10.3 | 7.0 | 49.7 | 4.0 | 11.0 | 7.0 |
| 8 | C$_{21}$H$_{19}$IN$_4$O$_2$S.2HCl | 43.4 | 3.8 | 9.6 | | 42.8 | 3.6 | 9.5 | |
| 9 | C$_{21}$H$_{19}$N$_5$O$_4$S.HCl.½H$_2$O | 52.0 | 4.5 | 14.6 | 7.5 | 52.2 | 4.4 | 14.5 | 7.3 |
| 10 | C$_{22}$H$_{23}$N$_5$O$_2$S.2HCl | 53.5 | 5.3 | 11.5 | 14.5 | 53.4 | 5.1 | 11.3 | 14.3 |
| 11 | C$_{23}$H$_{23}$N$_5$O$_4$S.HCl | 55.0 | 5.0 | 13.6 | 7.3 | 55.0 | 4.8 | 13.9 | 7.1 |
| 12 | C$_{22}$H$_{22}$N$_4$O$_2$S.HCl.½H$_2$O | 58.8 | 5.2 | 12.0 | 8.1 | 58.4 | 5.1 | 12.4 | 7.8 |
| 13 | C$_{22}$H$_{22}$N$_4$O$_3$S.HCl | 55.2 | 4.9 | 11.5 | | 55.3 | 5.3 | 11.8 | |
| 15 | C$_{23}$H$_{23}$N$_5$O$_3$S.2HCl | 53.2 | 5.2 | 13.5 | | 52.9 | 4.8 | 13.4 | |
| 16 | C$_{23}$H$_{24}$N$_4$O$_2$S.HCl | 59.4 | 5.5 | 12.0 | 8.1 | 59.2 | 5.6 | 12.0 | 7.6 |
| 17 | C$_{23}$H$_{24}$N$_4$O$_3$S.HCl½H$_2$O | 57.6 | 5.8 | 11.7 | 7.3 | 57.3 | 5.4 | 11.6 | 7.4 |
| 18 | C$_{22}$H$_{21}$FN$_4$O$_2$S.HCl | 57.2 | 4.7 | 11.9 | 7.4 | 57.3 | 4.8 | 12.2 | 7.7 |
| 19 | C$_{22}$H$_{21}$ClN$_4$O$_2$S.HCl | 54.8 | 5.0 | 11.4 | 14.7 | 55.3 | 4.7 | 11.7 | 14.9 |
| 20 | C$_{22}$H$_{21}$ClN$_4$O$_3$S.HCl | 53.7 | 4.9 | 11.4 | 14.3 | 53.5 | 4.5 | 11.4 | 14.4 |
| 21 | C$_{22}$H$_{21}$BrN$_4$O$_2$.HCl | 50.2 | 4.8 | 10.3 | 6.6 | 50.6 | 4.3 | 10.7 | 6.8 |
| 22 | C$_{23}$H$_{24}$N$_4$O$_3$S.2HCl | 54.3 | 5.5 | 11.1 | 13.5 | 54.2 | 5.1 | 11.0 | 13.9 |
| 23 | C$_{23}$H$_{22}$ClN$_5$O$_3$S.HCl | 52.8 | 4.8 | 13.2 | 13.2 | 53.1 | 4.5 | 13.5 | 13.6 |
| 24 | C$_{24}$H$_{25}$N$_5$O$_3$S.HCl | 57.3 | 5.4 | 14.0 | 7.5 | 57.6 | 5.2 | 14.0 | 7.1 |
| 25 | C$_{23}$H$_{24}$N$_4$O$_2$S.HCl.½H$_2$O | 58.8 | 6.1 | 11.6 | 7.6 | 59.2 | 5.6 | 12.0 | 7.6 |
| 26 | C$_{23}$H$_{24}$N$_4$O$_4$S.HCl | 56.2 | 5.2 | 11.2 | 7.4 | 56.5 | 5.2 | 11.5 | 7.3 |
| 27 | C$_{22}$H$_{22}$N$_4$O$_3$S.HCl | 57.1 | 5.7 | 12.0 | 7.9 | 57.5 | 5.1 | 12.2 | 7.7 |
| 28 | C$_{22}$H$_{21}$BrN$_4$O$_3$S.HCl | 49.1 | 4.5 | 10.5 | 6.7 | 49.1 | 4.1 | 10.4 | 6.6 |
| 29 | C$_{23}$H$_{24}$N$_4$O$_3$S.HCl | 58.1 | 5.6 | 11.9 | 7.6 | 58.4 | 5.3 | 11.9 | 7.5 |
| 30 | C$_{23}$H$_{24}$N$_4$O$_4$S.HCl | 56.4 | 5.5 | 11.6 | 7.3 | 56.4 | 5.2 | 11.5 | 7.3 |

TABLE II-continued

Elemental Analyses for the Compounds of Table I

| | | Found | | | | Calculated | | | |
|---|---|---|---|---|---|---|---|---|---|
| No. | Formula | C | H | N | Cl | C | H | N | Cl |
| 31 | $C_{24}H_{26}N_4O_4S.HCl$ | 57.6 | 5.8 | 11.3 | 7.4 | 57.3 | 5.4 | 11.1 | 7.1 |
| 32 | $C_{22}H_{22}N_4O_2S.HCl.\frac{1}{2}H_2O$ | 58.8 | 5.7 | 12.1 | 7.9 | 58.5 | 5.4 | 12.4 | 7.9 |
| 33 | $C_{22}H_{21}ClN_4O_2S.HCl$ | 55.0 | 5.0 | 11.4 | 15.0 | 55.3 | 4.7 | 11.7 | 14.9 |
| 34 | $C_{23}H_{24}N_4O_2S.HCl.\frac{1}{2}H_2O$ | 58.9 | 6.2 | 11.9 | 7.8 | 59.3 | 5.6 | 12.0 | 7.6 |
| 35 | $C_{23}H_{24}N_4O_3S.HCl$ | 58.0 | 5.3 | 11.9 | 7.9 | 58.4 | 5.3 | 11.9 | 7.5 |
| 36 | $C_{24}H_{25}N_5O_3S.2HCl$ | 53.8 | 5.0 | 12.5 | 13.0 | 53.7 | 5.1 | 13.0 | 13.2 |
| 37 | $C_{23}H_{23}FN_4O_2S.HCl.\frac{1}{2}H_2O$ | 56.8 | 6.1 | 11.1 | 7.4 | 57.1 | 6.2 | 11.6 | 7.3 |
| 38 | $C_{23}H_{23}ClN_4O_2S.2HCl$ | 52.4 | 5.1 | 10.6 | 20.2 | 52.3 | 4.8 | 10.6 | 20.2 |
| 39 | $C_{23}H_{23}ClN_4O_3S.2HCl$ | 51.3 | 4.7 | 10.1 | | 50.8 | 5.5 | 10.3 | |
| 40 | $C_{24}H_{24}ClN_5O_3S.HCl$ | 53.7 | 5.0 | 13.0 | 13.2 | 53.9 | 4.7 | 13.1 | 13.3 |
| 41 | $C_{24}H_{26}N_4O_3S.HCl$ | 58.9 | 5.7 | 11.7 | 7.6 | 59.2 | 5.6 | 11.5 | 7.3 |
| 42 | $C_{24}H_{26}N_4O_2S.HCl$ | 60.9 | 6.3 | 11.5 | 7.5 | 61.2 | 5.8 | 11.9 | 7.5 |
| 43 | $C_{24}H_{26}N_4O_4S.HCl$ | 57.6 | 5.3 | 11.1 | 7.0 | 57.3 | 5.4 | 11.2 | 7.1 |
| 44 | $C_{25}H_{27}N_5O_3S.HCl$ | 58.0 | 5.8 | 13.6 | 7.1 | 58.4 | 5.5 | 13.6 | 6.9 |
| 45 | $C_{23}H_{24}N_4O_3S.HCl.\frac{1}{2}H_2O$ | 57.2 | 5.1 | 11.5 | | 57.3 | 5.4 | 11.6 | |
| 46 | $C_{24}H_{26}N_4O_3S.HCl$ | 58.9 | 5.9 | 11.3 | 7.5 | 59.2 | 5.6 | 11.5 | 7.3 |
| 47 | $C_{22}H_{23}N_4O_3P.HCl.H_2O$ | 54.9 | 5.6 | 12.1 | | 55.4 | 5.5 | 11.8 | |
| 48 | $C_{22}H_{22}BrN_4O_3P.HCl.\frac{1}{2}H_2O$ | 48.5 | 4.9 | 10.1 | 6.7 | 48.3 | 4.4 | 10.2 | 6.5 |
| 49 | $C_{23}H_{25}N_4O_3P.HCl$ | 64.2 | 6.0 | 13.1 | 8.2 | 64.5 | 6.1 | 13.1 | 8.3 |
| 50 | $C_{22}H_{20}N_4O_2.HCl.\frac{1}{2}H_2O$ | 63.0 | 5.5 | 13.2 | 8.7 | 63.2 | 5.3 | 13.4 | 8.5 |
| 51 | $C_{23}H_{22}N_4O_3.HCl$ | 62.8 | 5.3 | 12.5 | 7.8 | 62.9 | 5.3 | 12.8 | 8.1 |
| 52 | $C_{23}H_{22}N_4O_2.HCl$ | 65.6 | 5.8 | 12.8 | 8.4 | 65.3 | 5.5 | 13.3 | 8.4 |
| 53 | $C_{22}H_{19}FN_4O_2.HCl$ | 62.2 | 4.9 | 13.1 | 8.3 | 62.0 | 4.7 | 13.2 | 8.2 |
| 54 | $C_{22}H_{19}ClN_4O_2.HCl$ | 59.3 | 4.6 | 12.5 | 16.5 | 59.6 | 4.6 | 12.6 | 16.0 |
| 55 | $C_{22}H_{19}BrN_4O_2.HCl$ | 54.1 | 4.4 | 11.6 | 7.4 | 54.2 | 4.1 | 11.5 | 7.3 |
| 56 | $C_{23}H_{21}ClN_4O_2.2HCl$ | 56.4 | 5.0 | 11.1 | 20.7 | 55.9 | 4.7 | 11.3 | 21.5 |
| 57 | $C_{23}H_{21}BrN_4O_2.HCl$ | 55.1 | 4.7 | 11.2 | | 55.0 | 4.4 | 11.2 | |
| 58 | $C_{23}H_{22}N_4O_2.HCl.1.5H_2O$ | 61.5 | 5.9 | 12.7 | | 61.4 | 5.8 | 12.5 | |
| 59 | $C_{23}H_{22}N_4O_2.HCl$ | 65.2 | 5.7 | 13.1 | 8.6 | 65.3 | 5.5 | 13.3 | 8.4 |
| 60 | $C_{26}H_{22}N_4O_2S.HCl$ | 63.4 | 4.6 | 11.5 | 7.4 | 63.6 | 4.7 | 11.4 | 7.2 |
| 61 | $C_{27}H_{24}N_4O_3S.HCl$ | 62.1 | 5.1 | 10.8 | 6.8 | 62.2 | 4.8 | 10.8 | 6.8 |
| 62 | $C_{26}H_{23}N_5O_2S.HCl.\frac{1}{2}H_2O$ | 60.4 | 4.9 | 13.7 | | 60.6 | 4.9 | 13.6 | |
| 63 | $C_{26}H_{22}BrN_5O_2S.HCl$ | 54.5 | 4.2 | 10.8 | 6.4 | 53.4 | 4.0 | 11.0 | 6.8 |
| 64 | $C_{27}H_{25}N_5O_2S.HCl.\frac{1}{2}H_2O$ | 60.8 | 5.2 | 13.1 | 6.6 | 61.3 | 5.0 | 13.2 | 6.7 |
| 65 | $C_{27}H_{25}N_5O_3S.HCl.H_2O$ | 58.1 | 5.2 | 12.4 | | 58.5 | 5.1 | 12.6 | |
| 66 | $C_{27}H_{22}N_4O_2.HCl$ | 69.1 | 5.2 | 12.0 | 7.7 | 68.9 | 4.9 | 11.9 | 7.5 |

The following Examples illustrate the preparation of compounds of the general formula (I).

EXAMPLE A

Preparation of compound 32 of Table I via the method of Scheme I

3-Dimethylamino-4-nitroacetanilide (X, A=B=CH$_3$)

A suspension of 3-chloro-4-nitroacetanilide (IX,X=Cl) (6.8 g) in 40% aqueous dimethylamine (45 ml) was heated at 80° C. with stirring for 3 h, and then diluted with water (50 ml). After cooling for 15 h at 0° C., the solid was collected and crystallized from aqueous ethanol, m.p. 66°–67° C.

3-Dimethylamino-4-nitroaniline (XI, A=B=CH$_3$)

A solution of the above acetanilide (5 g) in a mixture of 4N aqueous HCl (25 ml) and ethanol (25 ml) was heated under reflux for 3 h. Evaporation of the solvents, followed by basification and crystallization of the residue from aqueous ethanol gave the diamine, m.p. 114°–115° C.

3-Dimethylamino-4-nitromethanesulfonanilide (XII, A=B=CH$_3$, Y=SO$_2$CH$_3$)

A solution of the above 3-dimethylamino-4-nitroaniline (4.40 g) in pyridine (20 ml) was treated at 0° C. with methanesulfonyl chloride (2.09 ml). The mixture was kept at 20° C. for 4 h and excess solvent was removed under reduced pressure. The residue was triturated with water to give a solid which was extracted with 1N aqueous sodium hydroxide. Neutralization of this filtered solution precipitated the sulfonamide, which was crystallized from aqueous ethanol, m.p. 160°–161° C.

Compound 32 of Table I

A hot solution of 3-dimethylamino-4-nitromethanesulfonanilide (3.0 g) in 50% aqueous ethanol (100 ml) containing potassium hydrogen carbonate (11.5 g) was treated over a 5 min period with sodium hydrosulfite (9.05 g) dissolved in water (70 ml). The reaction mixture was then heated under reflux until the colour of the solution had been completely discharged. Evaporation of all solvents in vacuo gave a residue that was extracted with boiling benzene to give the o-phenylenediamine derivative (III, A=B=CH$_3$).

Solutions of this diamine and 9-chloroacridine in methanol were mixed and the coupling reaction was initiated with a trace of HCl. The solution was concentrated to small volume and ethyl acetate added until crystallization of the hydrochloride salt of the product began.

Compounds 33 to 44 of Table I were prepared according to the procedure of Example A by replacing 9-chloroacridine by the appropriately substituted 9-chloroacridines.

EXAMPLE B

Preparation of compound 51 of Table I via the method of Scheme I 3-(2-Hydroxyethylamino)-4-nitroaniline (XI, A=H, B=CH$_2$CH$_2$OH)

3-Chloro-4-nitroacetanilide (IX, X=Cl) (4.0 g) and ethanolamine (8.0 g) were heated together at 100° C. for 10 hours, then cooled and 2N HCl (65 ml) was added. Following thorough cooling the resulting solid was collected, washed well with hot water and crystallized from hot water; pure product being obtained as orange needles, m.p. 128°–129° C.

Methyl
N-[3-(2-hydroxyethylamino)-4-nitrophenyl]carbamate
(XII, A=H, B=CH$_2$CH$_2$OH, Y=CO$_2$CH$_3$)

A solution of 3-(2-hydroxyethylamino)-4-nitroaniline (50 g) in ethanol (50 ml) was treated at room temperature with methyl chloroformate (10 ml) and allowed to stand at room temperature for 8 hours. The reaction solution was then heated under reflux condition for 30 minutes, concentrated almost to dryness and shaken with excess water. The separated product was washed well with cold water and crystallized from 10% aqueous ethanol; pure compound being obtained as orange needles of m.p. 163°–164° C.

Compound 51 of Table I

Hydrogenation (H$_2$, Pd/C) of methyl N-[3-(2-hydroxyethylamino)-4-nitrophenyl]carbamate (1.5 g) in methanol (7.5 ml) followed by removal of the catalyst provided a methanolic solution of crude methyl N-[4-amino-3-(2-hydroxyethylamino)phenyl]carbamate (V, A=H, B=CH$_2$CH$_2$OH). To this was added 9-chloroacridine (1.20 g), the mixture was stirred until homogeneous, acid catalyst (12NHCl; 0.1 ml) was added and the solution was boiled for 15 minutes. Concentration of the solution followed by addition of ethyl acetate precipitated crude material. The solid was washed with acetone and recrystallized from methanol-ethyl acetate, pure product being obtained as red prisms of m.p. 240°–242° C.

Via the method of Scheme II
3-(N-Benzylhydroxyethylamino)-4-nitroaniline (XIV, B=CH$_2$CH$_2$OH)

The chloroacetanilide (IX, X=Cl) (10 g, 47 mM) was dissolved in dry N-benzylethanolamine (20 ml) and heated (with protection from moisture) for 45 h at 100° C. The resulting solution was diluted with ethanol (50 ml), and a solution of KOH (5 g) in water (30 ml) was added. After 30 min at reflux to remove the acetyl group, the ethanol was removed in vacuo and the acidified (dilute acetic acid) residue extracted with ethyl acetate. This was washed successively with dilute acetic acid, water, dilute KHCO$_3$ solution and brine, and the solvent removed under vacuum to give the crude amine, which was purified by elution from a silica gel column.

Dichloromethane—methanol (99:1) eluates removed non-polar impurities, and (95:5) eluates gave the pure compound as an oil (66% yield).

Methyl
N-[3-(2-hydroxyethylamino)-4-nitrophenyl]carbamate
(XII, A=H, B=CH$_2$CH$_2$OH, Y=CO$_2$CH$_3$)

A solution of the above compound in ethanol was treated at 20° C. with methyl chloroformate, and allowed to stand at 20° C. for 8 h, then heated under reflux for 30 min. Concentrated HCl was added to the cooled solution, which was then heated under reflux until TLC analysis showed complete removal of the benzyl group. The mixture was evaporated to dryness and the resulting solid recrystallized from aqueous ethanol to give the carbamate, m.p. 163°–164° C.; identical to the product obtained as detailed above by the Scheme I pathway. The carbamate was then converted to compound 51 of Table I as described above.

EXAMPLE C

Preparation of compound 1 of Table I via the method of Scheme II 3-(N-benzylmethylamino)-4-nitroaniline (XIV, B=CH$_3$)

The bromide (IX, X=Br) (8 g, 31 mM) was dissolved in dried (CaH$_2$) N-benzylmethylamine (15 ml) in a flask equipped with a CaCl$_2$ drying tube. The resulting solution was heated at 100° C. in a waterbath for 2 hours, and diluted with 50 ml of ethanol. A solution of 5 g of KOH in 30 ml of water was added and the mixture was heated under reflux for 30 minutes, when complete loss of the acetyl group was observed by TLC (CHCl$_3$—MeOH, (9:1). The ethanol was removed under vacuum and, after being acidified with dilute acetic acid, the residue was extracted with ethyl acetate. The organic layer was washed successively with dilute acetic acid, water, dilute KHCO$_3$ solution, and brine, and was dried over Na$_2$SO$_4$. Removal of the solvent under vacuum gave 7.8 g (98%) of the crude amine (XIV, B=CH$_3$) as an orange oil, which was crystallized from methanol m.p. 80°–81° C.

NOTE:
(i) the corresponding chloro compound may be used in the above reaction if the reaction time is increased to 48 h.
(ii) acid hydrolysis of the acetyl group leads to appreciable amounts of debenzylation.

N-(3-methylamino-4-nitrophenyl)methanesulfonamide
(XII, B=CH$_3$, Y=SO$_2$CH$_3$)

2.57 g (10 mmol) of the above crude amine was dissolved in the minimum volume of pyridine and after being cooled to 0° C. the solution was treated with 0.95 ml (1.2 equivalents) of methanesulfonyl chloride. The mixture was allowed to warm slowly to room temperature and after the reaction was complete (1–3 hours) the excess reagent was quenched by the addition of a small volume of water. The solvent was removed under vacuum and the residue was dissolved in a mixture of 25 ml of ethanol, 15 ml of water and 10 ml of concentrated hydrochloric acid. The mixture was then heated under reflux for 1 hour when complete debenzylation was observed by TLC (CHCl$_3$—MeOH; 9:1). The ethanol was removed under vacuum and the residue was dissolved in cold dilute NaOH solution. An insoluble oil was removed by treatment with charcoal-celite and, after filtration, the orange solution was acidified with dilute acetic acid to give a yellow solid which was collected by filtration and washed well with deionized water. Recrystallization from aqueous ethanol gave 1.9 g (78%) of the nitrosulfonamide (XII, B=CH$_3$, Y=SO$_2$CH$_3$) as either orange prisms or yellow needles depending upon the exact crystallization conditions, m.p. 191°–193° C.

NOTE:
Debenzylation was performed at this stage, because with the benzyl group present the sulfonamide (XV, B=CH$_3$, Y=SO$_2$CH$_3$), is an oil.

Compound 1 of Table I

The above sulfonamide (XII, B=CH$_3$, Y=SO$_2$CH$_3$) (1.0 g, 3.9 mM) was dissolved in warm methanol (100 ml) and hydrogenated over 5% Pd/C until H$_2$ uptake ceased (ca. 30 min). The resulting solution of III (A=H, B=CH$_3$) was quickly filtered and added to a suspension of 9-chloroacridine (0.8 g, 3.75 mM) in methanol (50 ml). A trace of HCl was added, and the mixture warmed to boiling for a few minutes, and concentrated to one quarter volume. Hot ethyl acetate (2-3 parts) was added, and the mixture left to crystallize. The resulting hydrochloride salt is pure, but if necessary may be recrystallized from methanol-ethyl acetate, m.p. 261°-263° C. Yield 85%.

Compounds 2 to 26 of Table I were prepared according to the procedure of Example C by replacing 9-chloroacridine by the appropriately substituted 9-chloroacridines.

EXAMPLE D

Preparation of Compound 45 of Table I via the method of Scheme II

Dimethyl N-[3-(N-benzylmethylamino)-4-nitrophenyl]-phosphoramidate (XV, B=CH$_3$, Y=P(O) (OCH$_3$)$_2$)

A stirred solution of 3.80 g (0.014 mol) of amine (XIV, B=CH$_3$; preparation given in Example B) in 30 ml of pyridine was treated dropwise with a large excess (0.20 mol) of freshly prepared dimethyl phosphorobromidate. The mixture was allowed to warm slowly to room temperature overnight and after being quenched with water the solvent was removed under vacuum and the residue was extracted with ethyl acetate. The organic layer was washed successively with aqueous methane-sulfonic acid, water, KHCO$_3$ solution and brine, and was dried over Na$_2$SO$_4$. Removal of the solvent gave the crude product which was extracted with benzene and treated with charcoal-celite to remove a polar impurity. The solution was filtered, to remove all traces of charcoal-celite, and the solvent was removed to give 2.05 g (40%) of (XII, B=CH$_3$, Y=P(O) (OCH$_3$)$_2$) as a yellow oil which slowly crystallized on standing and was recrystallized from aqueous methanol, m.p. 128° C.

Alternatively, this compound could be prepared by treatment of the amine (XIV, B=CH$_3$) (12.85 g, 50 mM) with a mixture of POCl$_3$ (75 ml) and pyridine (15 ml) at 0° C., dilution with petroleum ether. Refrigeration overnight gave the crude phosphoryl dichloride which was then reacted with excess sodium methoxide in methanol at 0° C. Neutralization with dilute acetic acid and removal of the methanol under vacuum was followed by extraction with ethyl acetate and washing with NaHCO$_3$ solution. Removal of solvent and recrystallization from methanol gave the phosphoramidate (XV) (3.38 g, 19%). Chromatography of the residues of silica gel afforded a further 5% of product.

Dimethyl N-(4-amino-3-methylaminophenyl)phosphoramidate (IV, A=H, B=CH$_3$)

A methanolic solution of XV, Y=P(O) (OCH$_3$)$_2$, B=CH$_3$) was hydrogenated over Pd on charcoal to give the o-phenylenediamine derivative (IV, A=H, B=CH$_3$).

The ready reduction of the nitro group was easily followed by decolorization of the solution, but hydrogenolysis of the benzyl group was much slower and was best followed by TLC (CHCl$_3$—MeOH, 9:1). No attempt was made to characterize the product (which was very susceptible to auto-oxidation), so after filteration to remove the Pd/C catalyst the solution was combined directly with a solution of 9-chloroacridine in methanol and treated with a few drops of concentrated HCl.

Compound 45 of Table I

Concentration of the methanol solution obtained above and dilution with ethyl acetate gave the hydrochloride salt, which was collected by filtration, washed with acetone and petroleum ether, and recrystallized from MeOH—EtOAc. The product was kept as the hydrochloride salt because of the susceptibility of the free base towards aerial oxidation.

Compound 46 of Table I was prepared according to the procedure of Example D by replacing 9-chloroacridine by 4-methyl-9-chloroacridine.

EXAMPLE E

Preparation of compound 27 of Table I via the method of Scheme III

3-Bromo-4-nitromethanesulfonanilide (XVII, X=Br, Y=SO$_2$CH$_3$)

A solution of 3-bromo-4-nitroaniline (XVI, X=Br) (4.50 g), obtained by mild acid hydrolysis of the acetanilide (IX, X=Br), was treated at 5° C. with methanesulfonyl chloride (1.86 ml), in pyridine (25 ml), left at room temperature for 12 hours and then heated at 100° C. for 15 minutes. The resultant solid following removal of excess solvent and trituration with water was extracted with 0.5N aqueous sodium hydroxide. Acidification (HCl) of the filtered solution gave the crude sulfonamide. Crystallization from aqueous ethanol provided pure product, m.p. 209°-210° C.

3-(2-Hydroxyethylamino-4-nitromethanesulfonanilide (XII, A=H, B=CH$_2$CH$_2$OH, Y=SO$_2$CH$_3$)

The above 3-bromo-4-nitromethanesulfonanilide (3.0 g) and ethanolamine (5.5 g) were heated together for 12 hours and then diluted with 1N aqueous HCl (90 ml). Following thorough cooling the crude product was collected. Crystallization from water and then ethyl acetate provided pure material, m.p. 152°-153° C.

Compound 27 of Table I

A solution of the above nitrocompound (2.30 g) in methanol (25 ml) was hydrogenated over palladium/C until hydrogen uptake ceased (15 min). The resultant solution of the o-phenylenediamine derivative (III, A=H, B=CH$_2$CH$_2$OH) was added to a methanolic solution of 9-chloroacridine and the coupling reaction initiated with a drop of HCl. The solution was then concentrated to small volume and ethyl acetate was added until crystallization of the hydrochloride salt of the product began.

Compounds 28 and 29 of Table I were prepared according to the procedure of Example E by replacing 9-chloroacridine by the appropriately substituted 9-chloroacridines.

Compounds 30 and 31 of Table I were prepared by procedures analogous to Example E for the preparation of the appropriate o-phenylenediamine derivative, and subsequent coupling with 9-chloroacridine or 4-methyl-9-chloroacridine.

EXAMPLE F

Preparation of compound 47 of Table I

Dimethyl N-[3-(N-benzylmethylamino)-4-nitrophenyl]phosphoramidate 12.85 g (0.05 mole) of 3-(N-benzylmethylamino)-4-nitroaniline in 30 ml CH₂Cl₂ was added to a mixture of 75 ml POCl₃ and 15 ml pyridine at 0° C. After being stirred for 1 h, the mixture was diluted with 400 ml of dry petroleum ether and stored at −10° C. overnight. The solvent was decanted off, and after being washed several times with dry petroleum ether the residue was dissolved in a methanolic solution of sodium methoxide at 0° C. The solution was neutralized with HOAc and the methanol was removed under vacuum. Workup in ethyl acetate gave an oil which crystallized on standing in cold methanol. Yield 3.38 g (19%), m.p. 128°–128.5° C.

Compound 47 of Table I

The above nitro compound was exhaustively hydrogenated over Pd/C to provide a solution of the diamine, which was used immediately for coupling with 9-chloroacridine as usual. Crystallization of the product from MeOH—EtOAc gave red product, m.p. 230° C.

Compounds 48 and 49 of Table I were prepared according to the procedure of Example F by replacing 9-chloroacridine by the appropriately substituted 9-chloroacridines.

EXAMPLE G

Preparation of compound 50 of Table I by the general method of Scheme II

Methyl N-[3-(N-benzylmethylamino)-4-nitrophenyl]carbamate

A stirred solution of 3-(N-benzylmethylamino)-4-nitroaniline (2.2 g, 8.5 mM) in dry dimethoxyethane (15 ml) and pyridine (4 ml) was treated dropwise with methyl chloroformate (10 mM) at 0° C. The mixture was allowed to warm slowly to 20° C. and after 3 h was quenched with water (5 ml). Volatile solvents were removed under vacuum and the residue was extracted with ethyl acetate. After successive washings with aqueous methanesulfonic acid, water, aqueous KHCO₃ and brine the organic layer was dried over Na₂SO₄. Removal of the solvent and chromatography of the residue on silica gel in ethyl acetate-petroleum ether (3:7) gave the product as a bright red oil (2.25 g, 84% yield).

Compound 50 of Table I

The above nitro compound in methanol was exhaustively hydrogenated over Pd/C. The resulting solution of diamine was immediately coupled with 9-chloroacridine as described previously to yield the product hydrochloride as red needles, m.p. 268° C.

Compounds 52–58 of Table I were prepared according to the procedure of Example G by replacing 9-chloroacridine by appropriately substituted 9-chloracridines.

Compound 59 of Table I was prepared by a procedure analogous to Exampel G for the preparation of the appropriate diamine, and subsequent coupling with 9-chloroacridine.

EXAMPLE H

Preparation of compound 60 of Table I by the method of Scheme II

N-(3-methylamino-4-nitrophenyl)benzenesulphonamide 2.5 g (9.7 mmol) of 3-(N-benzylmethylamino-4-nitroaniline in 15 ml dry pyridine was treated with 1.5 ml of benzenesulphonyl chloride at 0° C. and the mixture was then allowed to warm slowly to room temperature. After 3 h the pyridine was removed under vacuum and the residue was dissolved in 100 ml of 2N HCl in 65% aqueous ethanol. The mixture was then heated under reflux until only one compound was seen by TLC (CHCl₃—MeOH, 9:1). Concentration of the solution then gave crystals of N-(3-methylamino-4-nitrophenyl)-benzenesulphonamide 2.93 g, 98%, m.p. 172°–173.5° C.

Compound 60 of Table I

The above nitro compound was dissolved in methanol and hydrogenated over Pd/C. The resulting solution of diamine was immediately coupled within 0.95 equivalents of 9-chloroacridine as described previously, to provide the product hydrochloride as red needles, m.p. 294° C.

Compound 61 of Table I was prepared by a procedure analogous to Example H for the preparation of the appropriate diamine, and subsequent coupling with 9-chloroacridine.

EXAMPLE I

Preparation of compound 62 of Table I by the method of Scheme II

N-[3′-(N′-Benzylmethylamino)-4′-nitrophenyl]-4-acetamido benzenesulfonamide

Solid 4-acetamidobenzenesulfonyl chloride (4 g, 17.3 mM) was added slowly to a stirred solution of 3-(N-benzylmethylamino)-4-nitroaniline (3.72 g, 14.4 mM) in dry pyridine (15 ml) at 0° C. The mixture was stirred for a further 1 h and quenched with water. After removal of solvents under vacuum, the residue was extracted with EtOAc and the organic layer was washed successively with dilute HCl, water, aqueous KHCO₃ and brine. Drying and removal of the solvent followed by trituration of the residue with MeOH gave a solid product, m.p. 169° C. (5.2 g, 80%).

Compound 62 of Table I

The above nitro compound was suspended into ethanol and hydrogenated over Pd/C, resulting in a homogeneous solution of diamine which was immediately coupled with 9-chloroacridine as described previously to provide the N-acetate of the desired product.

This compound (1.4 g) was suspended in a mixture of ethanol (120 ml), c.HCL (30 ml) and water (50 ml), and heated under reflux until a homogeneous solution was obtained. The solvents were removed under vacuum and the residue was azeotroped to dryness with ethanol. Trituration with MeOH—EtOAc gave a solid which was recrystallized from the same solvent mixture to provide the product hydrochloride as red plates, m.p. 230° C.

Compounds 63 and 64 of Table I were prepared according to the procedure of Example I by replacing 9-chloroacridine by the appropriately substituted 9-chloroacridines.

Compound 65 of Table I was prepared by a procedure analogous to Example I for the preparation of the appropriate diamine, and subsequent coupling with 9-chloroacridine.

The compounds of general formula (I) and particularly the examples listed in Tables I and II, have antitumor activity in in vivo test systems, as shown by the data of Tables III and IV.

The compounds also show broad spectrum antibacterial activity. Specifically, compound 12 is active against the bacteria *Aerobacter aerogenes, Alcaligenes viscolactis, Escherichia coli, Bacillus subtilis, Sarcina lutea, Micrococcus lysodeikticus, Neisseria catarrhalis, Staphylococcus aureus, Xanthomonas phaseoli* and *Streptococcus faecalis*.

The following Tables III and IV give biological data for compounds 1, 3–13 and 15–66 whose physical data has been given in Tables I and II, together with corresponding data for m-AMSA (amsacrine, 4'-(9-acridinylamino)methanesulfon-m-anisidide). Table III gives P-388 in vivo leukemia data for all the compounds and Table IV gives Lewis lung in vivo data for selected compounds. The abbreviations used in Tables III and IV are:

No. The number given to the corresponding compound in Table I.

OD. The optimal drug dose (in milligrams per kilogram), administered as a solution in 0.1 ml of 30% v/v ethyl alcohol in water on days 1, 5 and 9 after tumor inoculation. The drug is administered as a soluble acid addition salt.

ILSmax. The percentage increase in lifespan of treated animals over that of control animals injected with tumour alone. The average survival of control mice was 11 days (for P388 leukemia) and 17 days (for Lewis lung carcinoma). ILS values greater than 20% (P388) and 40% (Lewis lung) are considered statistically significant.

ILS values marked with an asterisk (*) indicate tests which resulted in a proportion of long-term survivors.

Y. implies a significant value of drug activity at the stated dose.

N. implies no or not statistically significant activity.

P388. is the P388 Leukemia.

LL. is the Lewis lung carcinoma.

Both of these tumour lines were obtained as frozen cell stocks from Mason Research Inc., U.S.A., and are passaged interperitoneally in DBA-2 mice of either sex (P388) or subcutaneously in C57-B1 mice of either sex (Lewis lung), according to the standard methods (*Cancer Chemother. Reports*, 3, Part 3, p. 9, 1972).

Groups of six mice (F1 hybrids of DBA-2 male×C57-B1 female) of weight 20±1 g were injected intraperitoneally (P388) or intravenously (tail vein, Lewis lung) with $10^6$ tumour cells on day 0. When given in this manner, P388 cells grow diffusely in the peritoneal cavity, whereas the Lewis lung cells form distinct solid tumour nodules in the lungs.

TABLE III

Biological activity (P388 in vivo data) of Compounds of Table I

| No. | OD | ILSmax | active |
|---|---|---|---|
| 1 | 13.3 | 152* | Y |
| 3 | 5.9 | 83 | Y |
| 4 | 20 | 140* | Y |
| 5 | 45 | 157* | Y |
| 6 | 30 | 149* | Y |
| 7 | 20 | 94 | Y |
| 8 | 45 | 80 | Y |
| 9 | 5.9 | 70 | Y |
| 10 | 2.6 | 208* | Y |
| 11 | 13.3 | 135* | Y |
| 12 | 13.3 | 157* | Y |
| 13 | 30 | 118* | Y |
| 15 | 65 | 82 | Y |
| 16 | 5.9 | 92 | Y |
| 17 | 3.9 | 102 | Y |
| 18 | 45 | 152* | Y |
| 19 | 13.3 | 128* | Y |
| 20 | 45 | 105 | Y |
| 21 | 13.3 | 122 | Y |
| 22 | 13.3 | 122 | Y |
| 23 | 30 | 59 | Y |
| 24 | 13.3 | 94 | Y |
| 25 | 30 | 107 | Y |
| 26 | 45 | 84 | Y |
| 27 | 45 | 89 | Y |
| 28 | 65 | 117 | Y |
| 29 | 30 | 159* | Y |
| 30 | 45 | 84 | Y |
| 31 | 30 | 83 | Y |
| 32 | 166 | 212* | Y |
| 33 | 65 | 76 | Y |
| 34 | 45 | 141 | Y |
| 35 | 100 | 91 | Y |
| 36 | 100 | 67 | Y |
| 37 | 65 | 57 | Y |
| 38 | 65 | 157 | Y |
| 39 | 65 | 73 | Y |
| 40 | 100 | 50 | Y |
| 41 | 100 | 139* | Y |
| 42 | 100 | 73 | Y |
| 43 | 100 | 56 | Y |
| 44 | 20 | 79* | Y |
| 45 | 100 | 100* | Y |
| 46 | 45 | 152* | Y |
| 47 | 13.3 | 118 | Y |
| 48 | 8.9 | 77 | Y |
| 49 | 5.9 | 91 | Y |
| 50 | 30 | 132 | Y |
| 51 | 30 | 121 | Y |
| 52 | 8.9 | 86 | Y |
| 53 | 100 | 110 | Y |
| 54 | 65 | 104 | Y |
| 55 | 45 | 101 | Y |
| 56 | 30 | 151* | Y |
| 57 | 20 | 97 | Y |
| 58 | 13.3 | 114 | Y |
| 59 | 30 | 51 | Y |
| 60 | 45 | 117 | Y |
| 61 | 30 | 81 | Y |
| 62 | 0.8 | 104 | Y |
| 63 | 1.8 | 115 | Y |
| 64 | 1.2 | 139 | Y |
| 65 | 1.8 | 50 | Y |
| 66 | 65 | 71 | Y |
| m-AMSA | 13.3 | 78 | Y |

TABLE IV

Lewis Lung Antitumour Activity of Selected Compounds of Table I

| No. | OD | ILS | active |
|---|---|---|---|
| 1 | 20 | 85 | Y |
| 12 | 13.3 | 159* | Y |
| 13 | 45 | 153 | Y |
| 18 | 45 | 143* | Y |
| 19 | 30 | 126 | Y |
| 32 | 66 | >250 (all cured) | Y |
| 34 | 45 | 235* | Y |
| 35 | 100 | >250 (all cured) | Y |
| 38 | 150 | >250 (all cured) | Y |

TABLE IV-continued

Lewis Lung Antitumour Activity of Selected Compounds of Table I

| No. | Lewis Lung OD | ILS | active |
|---|---|---|---|
| 41 | 100 | 168* | Y |
| 44 | 30 | 128* | Y |
| 50 | 30 | 122* | Y |
| 56 | 20 | 100 | Y |
| 57 | 30 | 82* | Y |
| 58 | 8.9 | 48* | Y |
| m-AMSA | 13.3 | 38 | Y/N |

It is clear from the data of Tables III and IV that the o-phenylenediamine compounds are potent antitumour agents, giving significant levels of life extension when tested against the P388 leukemia system. Many of the compounds also show significant levels of activity against the Lewis lung tumour, when this tumour is implanted intravenously and is growing as solid tumour nodules in the lung. In contrast the prior art compound m-AMSA (amsacrine) shows minimal activity (ILS 38%), and in fact by the criteria established for this tumour is strictly inactive (required ILS of 40% for statistical significance).

The compounds generally also show a broad spectrum of antibacterial properties, and are active in a number of cultured tumour cell lines, including lines originating from human colon and breast tumours.

These compounds are thus indicated for use as antitumour agents, and the present invention also provides pharmaceutical compositions having antitumour activity and comprising at least one compound of general formula (I) or a pharmaceutically acceptable acid addition salt thereof, and one or more pharmaceutically acceptable carriers or diluents.

The present invention further provides a method for treating tumours in a patient which comprises administering to the patient an antitumour effective amount of a compound of the general formula (I) or a pharmaceutically acceptable acid addition salt thereof.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially nontoxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, following by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, anti-bacterial and anti-fungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. "Dosage unit form" as used herein refers to physically discreet units suitable as unitary dosages for the mammalian subjects to be treated; each unit containing a predetermined quantity of active material calculated to produce the desired therapeutic effect in association with the required pharmaceutical carrier. The specifications for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:

1. A compound represented by the general formula (I):

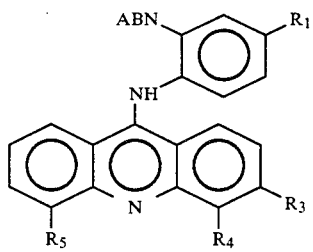

in which $R_1$ represents

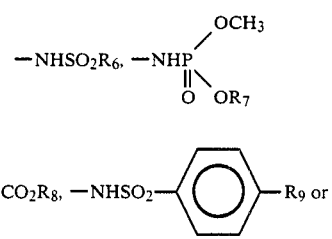

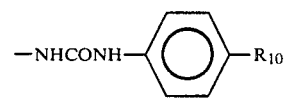

A and B each represent H or a lower alkane optionally substituted with amino and/or hydroxyl groups, except that A and B are not both H; $R_3$ represents H, $OCH_3$, $CH_3$, halogen, $NH_2$, $NO_2$, $NHCH_3$, $N_3(CH_3)_2$, $N_3$, $NHCOCH_3$, $NHCOOCH_3$, $N(CH_3)COOCH_3$, $CONH_2$ or $CONHCH_3$; $R_4$ represents H, alkyl, O-alkyl, $CONH_2$, $CONHCH_3$ or $CONHCH_2CONHCH_3$, except that $R_3$ and $R_4$ taken together can represent —C=CH—CH=N—; $R_5$ represents H, alkyl, O-alkyl, $CONH_2$, $CONHCH_3$ or $CONH_2CH_2CONHCH_3$; $R_6$ represents lower alkyl; $R_7$ represents $CH_3$ or $C_6H_5$ (phenyl); $R_8$ represents lower alkyl or $C_6H_5$ (phenyl); $R_9$ represents H, $NHCOCH_3$, $NH_2$ or $N=CHN(CH_3)_2$; and $R_{10}$ represents H or $NH_2$; or an acid addition salt thereof.

2. A compound according to claim 1 in which A represents H, B represents $CH_3$, $R_1$ represents $NHSO_2CH_3$, $R_3$ represents H, $CH_3$, $OCH_3$ or halogen, and $R_4$ and $R_5$ each represent H, $CH_3$ or $OCH_3$.

3. A compound according to claim 2 in which $R_3$ represents H, $CH_3$, F or Cl, $R_4$ represents H, and $R_5$ represents $CH_3$.

4. A compound according to claim 1 in which A and B both represent $CH_3$, $R_1$ represents $NHSO_2CH_3$, $R_3$ represents H, $CH_3$, $OCH_3$ or halogen, and $R_4$ and $R_5$ each represent H, $CH_3$, $OCH_3$ or $CONHCH_3$.

5. A compound according to claim 4 in which $R_3$ represents H or $OCH_3$, $R_4$ represents H or $CH_3$, and $R_5$ represents H, $CH_3$ or $CONHCH_3$.

6. A compound according to claim 1 in which A represents H, B represents $CH_3$, $R_1$ represents $NHCO_2CH_3$, $R_3$ represents H or $CH_3$, $R_4$ represents H, and $R_5$ represents H or $CH_3$.

7. A compound according to claim 2 in which A represents H, B represents $CH_3$, $R_1$ represents $NHSO_2CH_3$, and $R_3$, $R_4$ and $R_5$ all represent H.

8. A compound according to claim 2 in which A represents H, B represents $CH_3$, $R_1$ represents $NHSO_2CH_3$, $R_3$ and $R_5$ both represent H, and $R_4$ represents $CH_3$.

9. A compound according to claim 2 in which A represents H, B represents $CH_3$, $R_1$ represents $NHSO_2CH_3$, $R_3$ and $R_5$ both represent H, and $R_4$ represents $OCH_3$.

10. A compound according to claim 2 in which A represents H, B represents $CH_3$, $R_1$ represents $NHSO_2CH_3$, $R_3$ represents F, $R_4$ represents H, and $R_5$ represents $CH_3$.

11. A compound according to claim 2 in which A represents H, B represents $CH_3$, $R_1$ represents $NHSO_2CH_3$, $R_3$ represents Cl, $R_4$ represents H, and $R_5$ represents $CH_3$.

12. A compound according to claim 4 in which A and B both represent $CH_3$, $R_1$ represents $NHSO_2CH_3$, and $R_3$, $R_4$ and $R_5$ all represent H.

13. A compound according to claim 4 in which A and B both represent $CH_3$, $R_1$ represents $NHSO_2CH_3$, $R_3$ and $R_5$ both represent H, and $R_4$ represents $CH_3$.

14. A compound according to claim 4 in which A and B both represent $CH_3$, $R_1$ represents $NHSO_2CH_3$, $R_3$ and $R_5$ both represent H, and $R_4$ represents $OCH_3$.

15. A compound according to claim 4 in which A and B both represent $CH_3$, $R_1$ represents $NHSO_2CH_3$, $R_3$ represents Cl, $R_4$ represents H, and $R_5$ represents $CH_3$.

16. A compound according to claim 4 in which A and B both represent $CH_3$, $R_1$ represents $NHSO_2CH_3$, $R_3$ represents $OCH_3$, $R_4$ represents H, and $R_5$ represents $CH_3$.

17. A compound according to claim 4 in which A and B both represent $CH_3$, $R_1$ represents $NHSO_2CH_3$, $R_3$ represents H, $R_4$ represents $CH_3$, and $R_5$ represents $CONHCH_3$.

18. A compound according to claim 6 in which A represents H, B represents $CH_3$, $R_1$ represents $NHCO_2CH_3$, and $R_3$, $R_4$ and $R_5$ all represents H.

19. A compound according to claim 1 in which A represents H, B represents $CH_3$, $R_1$ represents $NHCO_2CH_3$, $R_3$ represents Cl, $R_4$ represents H, and $R_5$ represents $CH_3$.

20. A compound according to claim 1 in which A represents H, B represents $CH_3$, $R_1$ represents $NHCO_2CH_3$, $R_3$ represents Br, $R_4$ represents H, and $R_5$ represents $CH_3$.

21. A compound according to claim 1 in which A represents H, B represents $CH_3$, $R_1$ represents $NHCO_2CH_3$, $R_3$ and $R_5$ both represent H, and $R_4$ represents $CH_3$.

22. A pharmaceutical composition having activity against leukemia and Lewis lung carcinoma which comprises at least one compound of the general formula (I) defined in claim 1, or a pharmaceutically acceptable acid addition salt thereof, and one or more pharmaceutically acceptable carriers or diluents.

23. A method for treating leukemia and Lewis lung carcinoma which comprises administering to a patient an effective amount of a compound of the general formula (I) as defined in claim 1, or a pharmaceutically acceptable acid addition salt thereof.